US006992762B2

(12) United States Patent
Long et al.

(10) Patent No.: US 6,992,762 B2
(45) Date of Patent: Jan. 31, 2006

(54) METHOD AND APPARATUS FOR TIME RESOLVED OPTICAL IMAGING OF BIOLOGICAL TISSUES AS PART OF ANIMALS

(75) Inventors: William F. Long, Quebec (CA); Yves Bérubé-Lauzière, Sherbrooke (CA); David J. Hall, Montrel (CA); Laura McIntosh, Saint-Laurent (CA)

(73) Assignee: ART Advanced Research Technologies Inc., Saint-Laurent (CA)

( * ) Notice: Subject to any disclaimer, the term of this patent is extended or adjusted under 35 U.S.C. 154(b) by 88 days.

(21) Appl. No.: 10/665,297

(22) Filed: Sep. 22, 2003

(65) Prior Publication Data

US 2004/0089817 A1 May 13, 2004

Related U.S. Application Data
(60) Provisional application No. 60/505,352, filed on Dec. 12, 2002.

(30) Foreign Application Priority Data
Nov. 11, 2002 (WO) ............................... PCT/IB02/04698

(51) Int. Cl.
*G01J 3/30* (2006.01)
*G01N 21/64* (2006.01)

(52) U.S. Cl. ..................... 356/317; 356/318; 250/458.1
(58) Field of Classification Search ......... 356/317–318, 356/417; 600/407; 250/458.1–461.2
See application file for complete search history.

(56) References Cited

U.S. PATENT DOCUMENTS

| | | | | |
|---|---|---|---|---|
| 5,772,588 A | * | 6/1998 | Miwa et al. | 600/310 |
| 5,962,852 A | * | 10/1999 | Knuettel et al. | 356/496 |
| 6,335,792 B1 | * | 1/2002 | Tsuchiya | 356/432 |
| 6,615,063 B1 | * | 9/2003 | Ntziachristos et al. | 600/312 |
| 6,662,042 B1 | * | 12/2003 | Grable | 600/473 |
| 2004/0073119 A1 | * | 4/2004 | Mycek et al. | 600/476 |

* cited by examiner

*Primary Examiner*—F. L. Evans
*Assistant Examiner*—Kara Geisel
(74) *Attorney, Agent, or Firm*—Kent Daniels; Ogilvy Renault LLP

(57) ABSTRACT

There is provided a method and system for collecting optical data for use in time resolved optical imaging wherein light is directionally propagated through free-space optics to impinge on a plurality of illumination at the surface of a biological tissue such as that comprised in small animals. Light re-emitted from the tissue is collected and directionally propagated through free space optics towards a detector to produce time resolved optical signals useful for optical image reconstructions.

40 Claims, 5 Drawing Sheets

METHOD AND APPARATUS FOR TIME RESOLVED OPTICAL IMAGING OF BIOLOGICAL TISSUES AS PART OF ANIMALS

This application claims benefit of provisional application 60/505,352, filled Dec. 12, 2002

CROSS-REFERENCE TO RELATED APPLICATIONS

This application claims priority under 35USC§119(e) of U.S. patent application Ser. No. 10/317,856 filed Dec. 12, 2002 the petition to convert to a provisional patent application in accordance with 35USC§111(b)(6) and 37CFR1.53 (c)(2) being filed concurrently herewith. This application is related to commonly assigned co-pending U.S. patent application Ser. No. 10/624,902 bearing agent docket number 15186-41US, the specification of which is hereby incorporated by reference.

TECHNICAL FIELD

The invention relates to the field of optical imaging of turbid media such as biological tissues as part of animals. More specifically, the invention relates to time resolved optical data acquisition for use in optical imaging.

BACKGROUND OF THE INVENTION

Different types of imaging techniques such as positron emission tomography (PET), magnetic resonance imaging (MRI) and ultrasound imaging are available that can non-invasively gather information from within biological tissues as a basis for image reconstruction. More recently, another imaging technique, namely optical imaging has been the subject of intense research and commercial development.

Optical imaging is based on the information that can be derived from the analysis of the signal resulting from the interaction of light with matter as it is propagated within an object. Optical imaging of turbid medium can be performed using three different approaches namely continuous wave (CW), time domain (TD) and frequency domain (FD). CW is the simplest and least expensive of the three techniques but provides only limited information with regards to the spatial distribution of internal optical attenuation of the object being imaged. TD and FD, by conveying information on the time required by photons to travel within the object (FD through the Fourier transform) are considered to be "time resolved" and can be used to calculat the spatial distribution of optical characteristics of the object, such as absorption and scatter coefficients, via well known photon diffusion equations (for a review paper on this topic, see the article by Hawrysz and Sevick-Muraca, Neoplasia, vol.2 No 5, pp388–417, 2000).

Optical imaging is particularly attractive in view of its non-invasiveness which permits the acquisition of in vivo information without damaging biological tissues. Furthermore the technique may be useful to monitor drug distribution, detect the presence of abnormalities within organs, or map physiological activities within mammals.

However, widespread utilization of optical imaging systems has been impeded by some undesirable characteristics of existing systems. For example, optical imaging devices often require cumbersome arrangements of optical fibers that are used to transport the light to and from the object. Such systems have been described for example by Ntziachristos and Weissleder in patent application WO 02/41769 and by Hillman et al. Phys. Med. Biol, 46 (2001)1117–1130. The type of arrangement for the optical components described in these references requires a time consuming alignment of the region of interest with the optic fibers used to illuminate the object and detect the optical signal. This type of arrangement is particularly problematic when imaging is performed on living tissues of mammals.

Ease of data acquisition and in particular ease of the positioning the object relative to the optic components is especially important in applications requiring high throughput such as in clinical settings or in research that make use of small mammals such as mice. In this respect, commercially available optical imaging systems for imaging small mammals have been developed. For example, a bioluminescence imaging system developed by Xenogen Corp. (Biophotonics, vol.9, No.7 pp48–51, 2002) has been designed to collect light emanating from small mammals. However, this imaging device suffers from certain disadvantages. For example, it requires the presence of bioluminescent molecules which have a spatially restricted biodistribution profile therefore greatly reducing the flexibility in imaging desired region of interests (ROI). Furthermore, the technique is limited by the number of luminescent molecules that are currently available. Moreover, the system does not allow time resolved data to be acquired.

In view of the above, it would be desirable to provide an optical imaging system for imaging turbid media such as biological tissues that allows time resolved optical data to be acquired with increased flexibility and efficiency.

SUMMARY OF THE INVENTION

According to one broad aspect of the invention there is provided a system and method for time resolved optical imaging of biological tissues as part of an animal. The design of the optical components of the present system allows a beam of light to be directionally propagated through air, that is to say through free-space optics, to impinge on desired points of illuminations in a region of interest (ROI) of the tissue. Light re-emitted from the tissue is collected at collection points and directionally propagated through air (i.e. through free-space optics) towards a detector. The fact that the light is propagated through air allows for a greater flexibility in scanning different ROI by eliminating the need for cumbersome fiber optics arrangements. Thus there is no need for directly contacting the animal with optical components thereby leaving sufficient space to manipulate or access the animal.

The optical design of the system permits illumination and light collection through air of nearby points in the ROI with minimal interference between the illumination beam, or the light reflected at the skin/air interface, and the collected light.

In one embodiment, there is provided a time resolved optical imaging method which comprises illuminating, at one or more wavelengths, a region of interest of an animal at a plurality of predetermined illumination points using a pulsed light beam. The beam is propagated through air and directed by using appropriate optical components to the illumination points A plurality of predetermined collection points are collected by optic components having a configuration enabling selective collection of light from well defined surface areas in the ROI. The collected light is then directed to a detector to produce an optical signal that can be used to generate an optical image using reconstruction algorithms.

In a further aspect of the invention there is provided a system for collecting optical data for use in time resolved imaging comprising one or more light sources for providing a light beam at one or more wavelengths, illuminating optic components for directionally propagating the beam through air such that a region of interest of the biological tissue within an animal is illuminated at a plurality of illumination points thereby injecting light into the tissue, collecting optic components for collecting light re-emitted at a plurality of predetermined collection points in the region of interest and for directionally propagating through air the collected light and a time correlated detector for detecting the collected light.

The system of the invention may advantageously be configured to acquire data for topographic or tomographic imaging. Topographic imaging is achieved by maintaining constant the distance between collection points and illumination points. Synchronized mirrors galvanometers are provided in the illumination and collection optics to achieve a constant distance between the illumination points and the detection points. Topographic data acquisition configurations can be used to obtain 2 dimensional (2D) or 3 dimensional (3D) images.

Tomographic imaging requires that light re-emitted from the animal be sampled at several different collection points/detection points configurations. The system of the present invention advantageously provides moveable mirrors in the illumination and collection optics that are independently controllable thereby providing means to achieve a plurality of illumination points/collection points configurations.

In another aspect there is provided a method and system for optical imaging of biological tissue containing fluorescent molecules. The tissue can be illuminated at an excitation wavelength while light re-emitted can be collected and detected at an emission wavelength. The system also enables detection of both the emission wavelength and the excitation wavelength.

BRIEF DESCRIPTION OF THE DRAWINGS

Further features and advantages of the present invention will become apparent from the following detailed description, taken in combination with the appended drawings, in which.

It will be noted that throughout the appended drawings, like features are identified by like reference numerals.

DESCRIPTION OF THE PREFERRED EMBODIMENT

The invention relates to the field of optical imaging of turbid media such as biological tissues as parts of animals. While the following description of the preferred embodiment provides examples that relate to imaging of small mammals such as mice, it will be appreciated that the method can also be applied to larger animals and in particular to laboratory animals such as dogs, pigs and primates.

Figure 1:
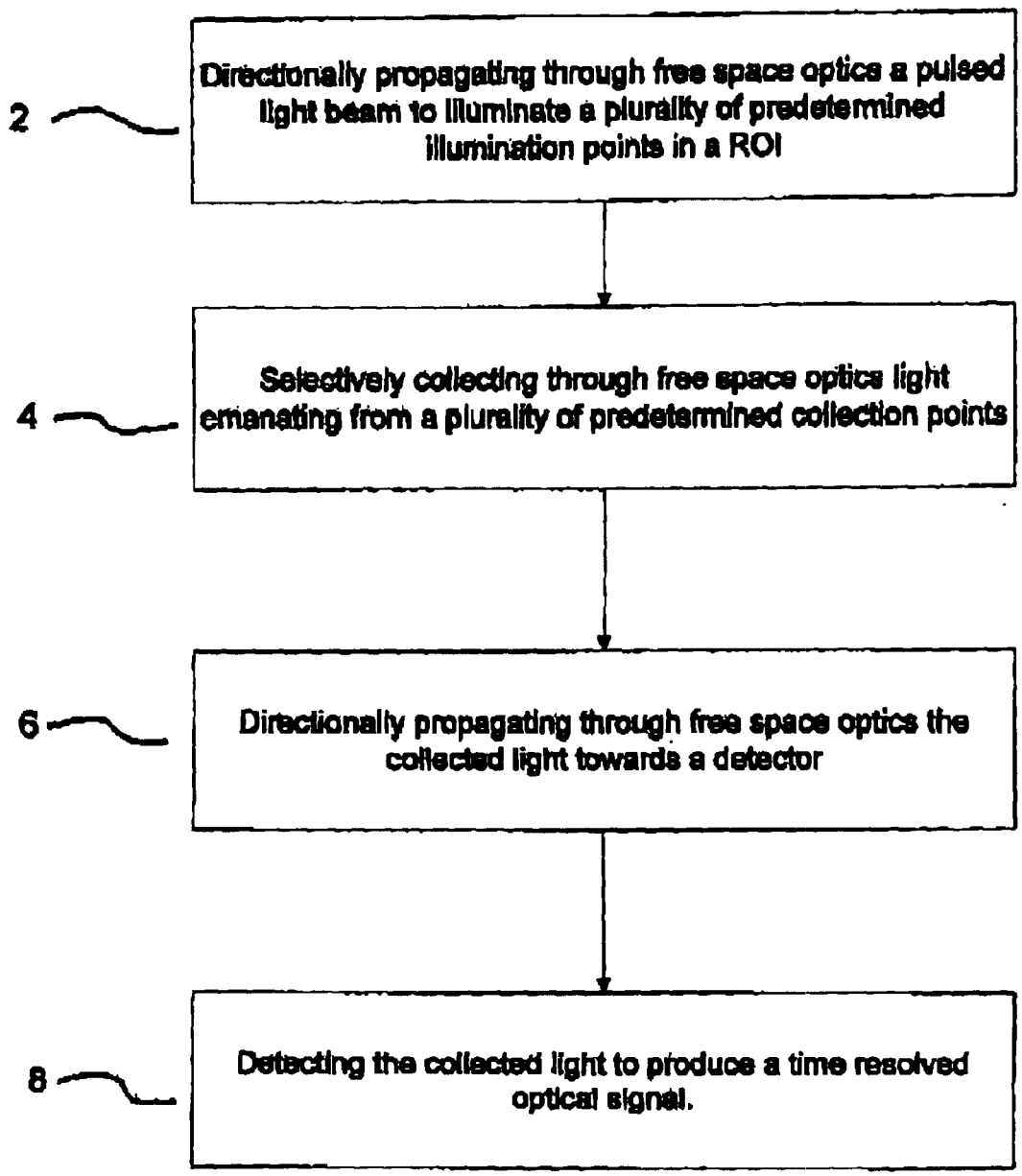
FIG. 1 is a flow chart diagram of an embodiment of the method of the instant invention.

With reference to FIG. 1 an embodiment of the method of the present invention for collecting optical data for use in time resolved optical imaging is generally described. At 2 pulsed light from a source of a selected intensity is directionally propagated in air (i.e. through free space optics) to illuminate a plurality of predetermined illumination points in a ROI of comprising biological tissue within an animal. The light emanating from a plurality of collection points after diffusion through the tissue is selectively collected through free space optics at 4 and directionally propagated through free space at 6 towards a detector. The collected light is finally measured at 8 using the detector to produce a time resolved optical signal. Light emanating from points other than that being sampled is optically excluded from detection.

The embodiments of the system used for collecting the optical data will now be described referring to small mammals as the object to be imaged but it will be appreciated that a wide variety of biological tissues may be amenable to optical imaging using the technique described herein. These can be but are not limited to breast tissue, brain, tumors and the like.

Figure 2:
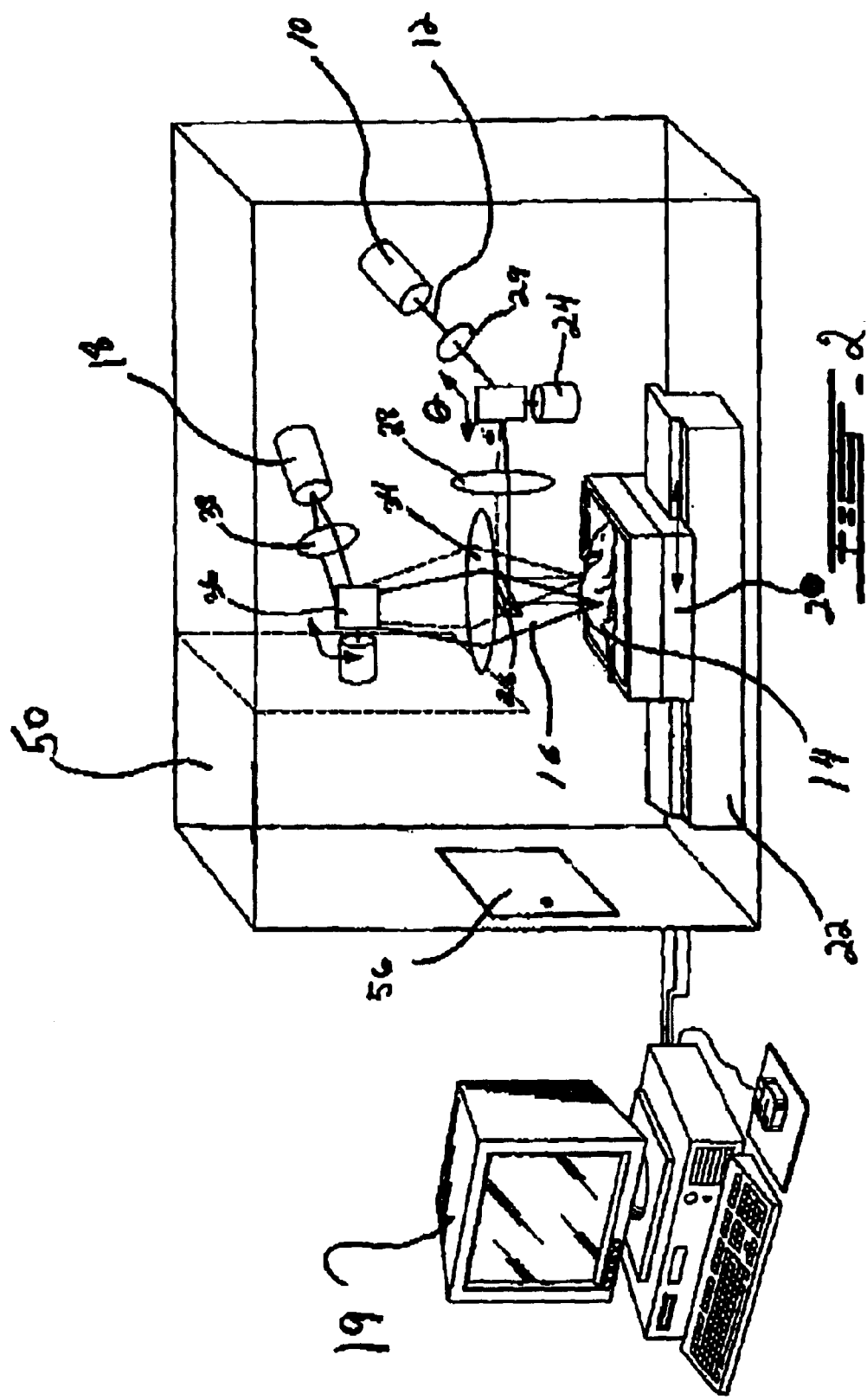
FIG. 2 is perspective view of an embodiment of the system of the invention.

A general schematic representation of the system of the present invention used for imaging small mammals is shown in FIG. 2. The system comprises a light source 10 capable of generating a beam of light 12 at one or more wavelengths, illuminating optics for directionally propagating the beam of light through air, i.e. through free space optics, to desired illumination points on the surface of the mammal 14, collecting optics for collecting the light 16 re-emitted from the mammal for directionally propagating the collected light to a detector 18, a moveable mammal supporting tray 20 mounted on a translational stage 22 and a computer 19 for controlling the source, the optics, the detector and the tray.

The illuminating optics comprises a moveable reflective mirror 24 which is preferably a mirror galvanometer. The beam is reflected by the mirror galvanometer at an angle θ and directed towards a thin angled mirror 26 which reflects the beam in a direction substantially perpendicular to the surface of the mammal being scanned. It can be appreciated that the partial rotation of the mirror galvanometer will modify the angle θ and direct the beam to a different point on the thin angled mirror and, consequently, to a different illumination point on the surface of the mammal. Successive partial rotations of the mirror galvanometer 24 thus produces a line scan substantially parallel to the thin angled mirror. Lens 28 is optionally provided and positioned between the mirror galvanometer and the thin angled mirror such that the mirror galvanometer is at the focal distance of the lens to provide telecentric imaging. Filters such as neutral density filter 29 may also be positioned between the source and mirror galvanometer 24 to adjust the intensity of the light beam.

Figure 3:
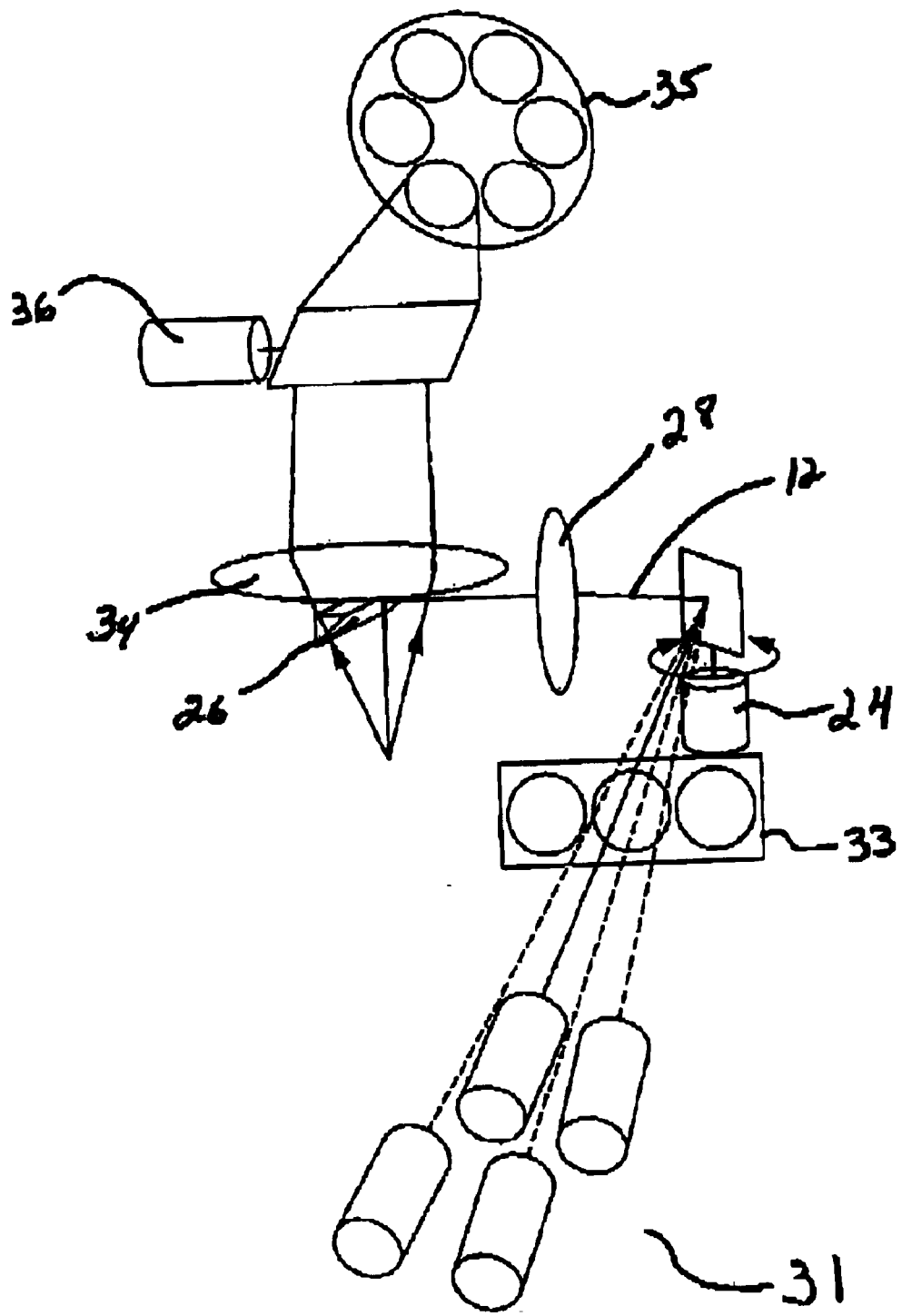
FIG. 3 is as schematic representation of an embodiment of the system in which the source comprises a plurality of lasers.
Figure 4:
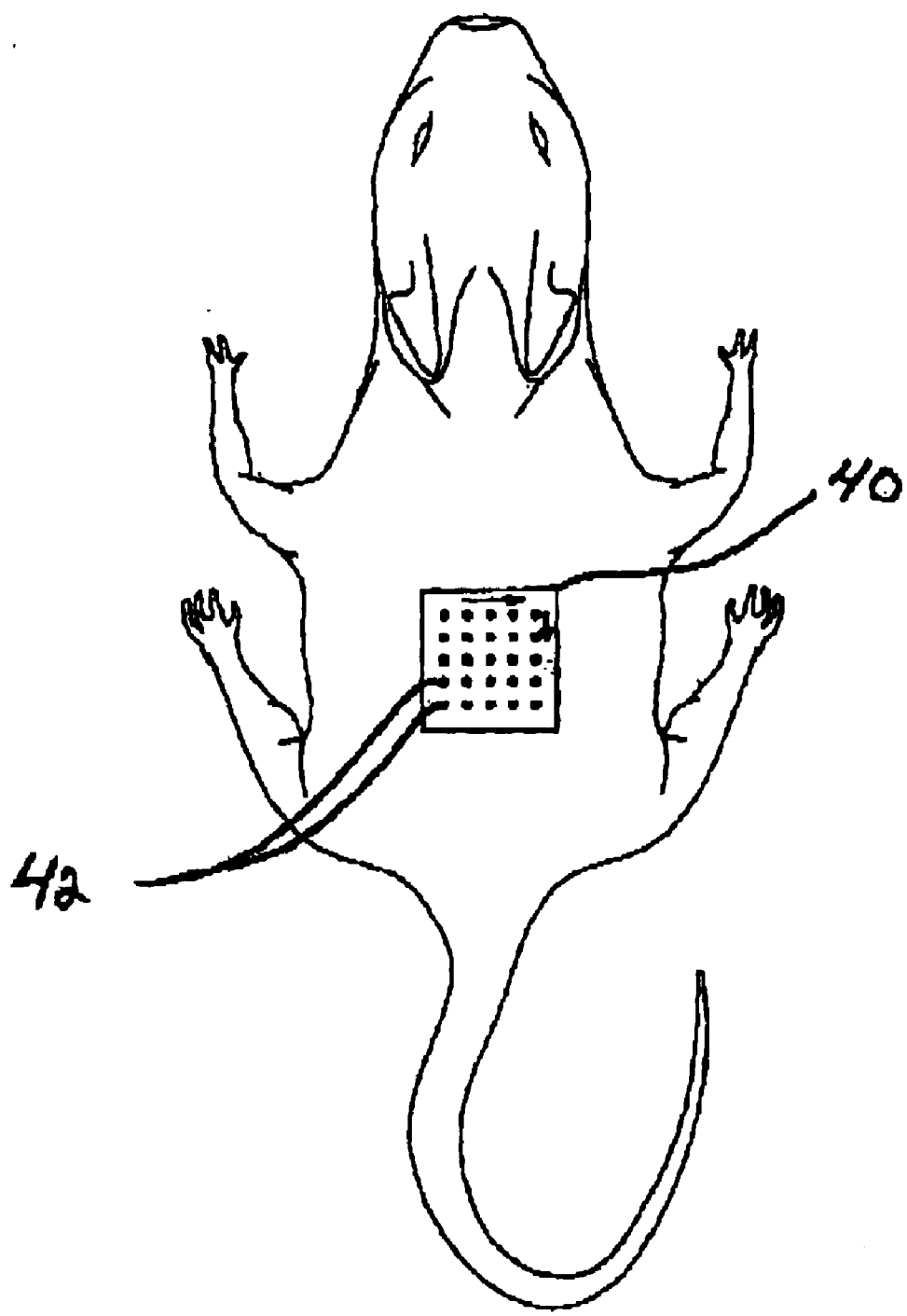
FIG. 4 schematically illustrates a raster scan pattern of illumination in a region of interest at the surface of a mammal.

In an aspect of the invention, the light source is preferably a variable intensity laser emitting light at a specific wavelength. To produce a multi-wavelengths illumination a collection of lasers 31, such as diode lasers, each emitting light at different wavelengths may be used (FIG. 3). Appropriate filters such as filters 33 and 35 may be positioned between the source and the mammal and between the re-emitted light and the detector for the selection of wavelengths or to adjust the intensity of the light. A switching or dichroic mirror system may be used for either sequential or simultaneous illumination of the mammal at different wavelengths. Alternatively, a unique multi-wavelengths source of light may also be used. In the latter case, ranges of wavelengths or specific wavelengths may be selected by using filters, gratings or the like, as is well known by persons skilled in the art.

The preferred intensity of the source is determined by Maximum Permissible Exposure (MPE) limits for biological tissues as established by regulatory instances. Standards for safe exposure are outlined, for example, in American National Standard for the safe use of lasers (ANSI Z 136.1–2000). For example, a laser emitting in the near infrared (NIR) should preferably be adjusted at a power of about 200 mW or less for non-invasive imaging of biological tissues such as that comprising humans and small mammals.

Tray 20 supports the mammal while it is being imaged. The mammal is preferably anesthetized for the duration of the data collection to reduce movements to a minimum. In alternative embodiment parts of or the whole animal could be mechanically restrained to reduce movements. Optionally the tray can be heated to maintain the body temperature of the mammal. Furthermore the tray can be displaced longitudinally on a translational stage 22 to position the mammal such that a plurality of line scans parallel to each other can be generated. This stepwise process is repeated a selected number of times to produce a raster scan of a region of interest (ROI). The raster scan can alternatively be achieved by longitudinally displacing the thin angled mirror 26. FIG. 3 illustrates an example of a raster scan pattern at the surface of a mammal. The user defined ROI 40 delimits the area to be scanned which comprises the predetermined illumination points 42. The arrangement of the optic components also permits other scanning patterns to be performed. It will be appreciated that the ROI may consist of the whole animal.

Light re-emitted from the mammal is collected by the collecting optics which comprise collecting lens 34, reflective mirror 36 which is preferably a mirror galvanometer and lens 38. Collecting lens 34 is located above the ROI and above the thin angled mirror. The angular position of the mirror 36 relative to the incoming light and the detector determines which collection point is being sampled since only part of the light (corresponding to a given collection point) impinging on the mirror is reflected at the proper angle to reach the detector. Selective detection of the light from a given collection point may be further enhanced by optically coupling the mirror galvanometer with lenses and/or pinholes.

The overall arrangement of the optics, which permits propagation of the light through air, allows for easy positioning and manipulation of the animal. Furthermore, since the system does not rely on optic fibers, a plurality of ROIs can be scanned without manipulating the animal simply by moving the tray so that a new ROI is brought in the focus of the optics. The movements of the tray can be controlled externally using the computer.

Upon impinging on the surface of the mammal, part of the light penetrates the skin and part is reflected at the air/skin boundary. The photons that are propagated within the mammal are absorbed and scattered, thereby producing a large number of photon paths. In biological tissues absorption may arise as a result of the presence of natural (endogenous) or exogenous chromophores while scattering is triggered by the presence of macromolecular structures such as proteins, lipids and the like which create refractive index inhomogeneities. The fraction of the light that is not absorbed ultimately exits the mammal by diffusing through the skin barrier at various distances from the illumination point. It can be appreciated that photons that have traveled deeper in the tissue will take a longer time to exit at the surface of the mammal. This provides the basis for the time resolved detection of the optical signal from which useful information about the optical properties of a region of interest can be extracted to be incorporated into image reconstruction algorithms. In optically homogeneous media the distance between the illumination point and the point at which given photons exit is related to the effective depth of the average path of the photons. Thus the greater the distance between the points the greater the depth. While biological tissues are not optically homogeneous the distance between illumination points and the point of photon exit can also be considered to be related to the depth of the average path of photons.

In a preferred embodiment the time resolved method used in the system of the present invention is time domain (TD). In TD measurements the source is briefly pulsed and the optical signal is detected as a function of time to generate a temporal point spread function (TPSF). The source is preferably a laser source capable of generating pulses characterized by a width in the picoseconds range. Time domain detectors such as time gated intensified CCDs (ICCDs), time correlated single photon counting devices(TCSPC's), ultrafast semiconductor detectors (avalanche and PIN photodiodes), photomultipliers and streak cameras can be used. In a preferred embodiment a TCSPC device is used in the system of the present invention. TCSPC's are capable of measuring the time taken by a photon to reach the detector as it travels through the illuminating optic, the tissue and the collecting optic. Time measurement is provided by a "clock" circuitry electronically coupling the source and the detector. Such circuits are well known in the art. TCSPC's are very sensitive and advantageously allows the use of low power sources to minimize damage to the tissue being scanned.

In an embodiment of the invention, attenuation measurements similar to measurements obtained using continuous wave can be generated using the system and method of the present invention by integrating the TPSF.

Statistically, the efficiency of detection, that is to say the ratio of the number of photons produced by the source and directed at a particular illumination point and the number of photons detected from a given collection point, is a function, inter alia, of the power of the light source and the distance from the illumination point at which the light is collected. The intensity of the source may be adjusted so that the flux of photons reaching the detector is optimized for the characteristics of the detector in a preferred embodiment, in which TD imaging of small mammals is performed using a TCSPC detection system, it is generally required that the probability of detecting a photon for each illumination light pulse be approximately 1% in order to avoid distortions caused by electronics dead-time losses in the temporal profile being measured as is well known by a person skilled in the art. The illumination duration (which is provided by the number of light pulses) directed at a given point on the mammal may vary in order to provide a sufficient number of detected photons to produce an adequate signal and yet keep the duration as short as possible to reduce the acquisition time. In accordance with the example of small animal imaging and using a light source emitting pulses at a frequency of 80 MHz, the power of the beam should be adjusted so that approximately $8 \times 10^5$ photons per second are detected. It will be appreciated that the selection of the appropriate frequency is based on, among other factors, the characteristics of the optical components, of the detector, of the tissue to be imaged and of the type of optical data that is desired.

The TPSF may also be generated by using a time gated intensified charged coupled device (ICCD). This type of detector can provide spatial resolution enabling simultaneous detection of optical signals emanating from different collection points. Furthermore when a source generating two or more wavelengths is used, the light collected at any given collection points can be divided into constituent wavelengths to produce two or more beams which can be directed to different detection positions of the ICCD. However, since the sensitivity of an ICCD is less than that of a TCSPC device, the intensity of the source should be adjusted accordingly while remaining below levels that could cause tissue damage.

In view of the low intensity levels of the source, especially in the case where TCSPC devices are used, and the high sensitivity of the detectors, the system and the mammal are placed in an enclosure such as a box 50. The box is preferably light tight to prevent any stray light from interfering with the measurements. The interior of the box can be accessed through door 56.

In order to construct an image of a region of interest (ROI) within the mammal, optical signals are obtained from a plurality of illumination/detection points within the ROI. The configuration of the illumination/detection points may vary depending of the type of image to be reconstructed. As will be explained below topographic and tomographic images can be generated with the system and method of the present invention and both require different illumination/detection configurations.

The position of the collection points relative to the illumination points is determined prior to the start of the acquisition and is a function of the desired depth of imaging in the region of interest. For planes of imaging that are close to the surface of the skin, the collection points are located near the illumination points since the deeper a photon travels, the lower is the probability of that photon being re-emitted near the illumination points, and conversely.

Thus in order to acquire topographic images collection points are maintained at a fixed distance from illumination points so as to gather information from substantially the same depth across the ROI. The mirror galvanometers comprised in the illuminating and the collecting optic may be synchronized to achieve rapid scanning with a constant illumination/detection points distance.

Tomographic data is obtained when the illumination and collection points are permuted so as to generate a plurality of illumination to collection points distances thereby obtaining information from different depths. By treating the data in an appropriate manner, tomographic images can be generated. For tomographic optical data acquisition the two mirror galvanometers 24 and 26 are preferably controlled independently in order to obtain multi-perspective data. Thus while the mirror galvanometer in the illumination optic directs the light at a desired illumination point, the mirror galvanometer in the collection optic may be programmed to sample light at a plurality of different collection points.

Figure 5:
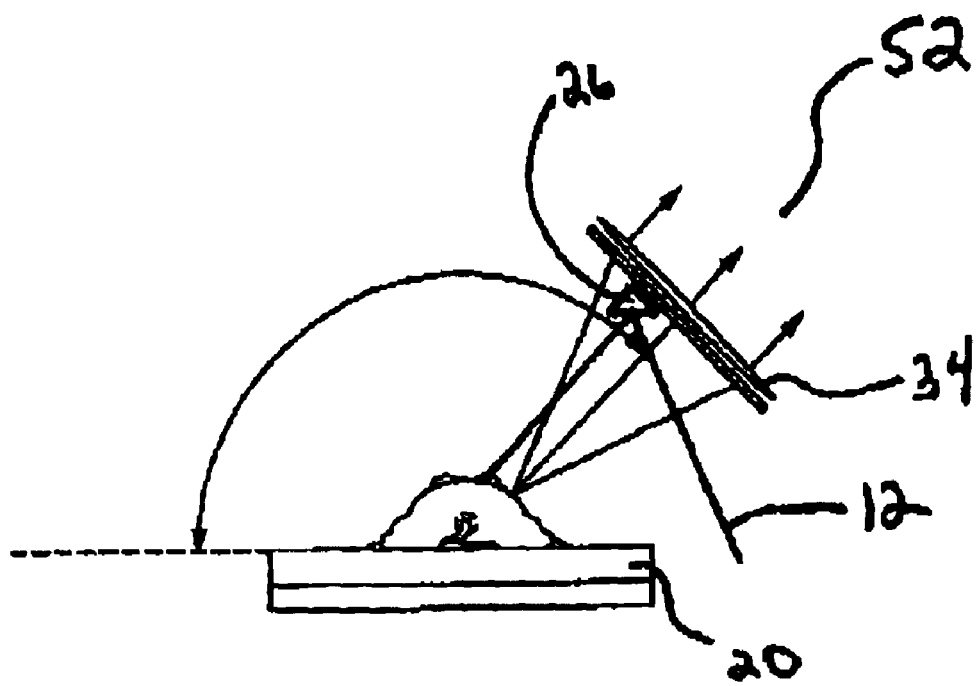
FIG. 5 a schematic representation of an embodiment of the system of the invention in which the optical components are mounted on a gantry to be rotated around the mammal to acquire data for tomographic imaging.
Figure 6:
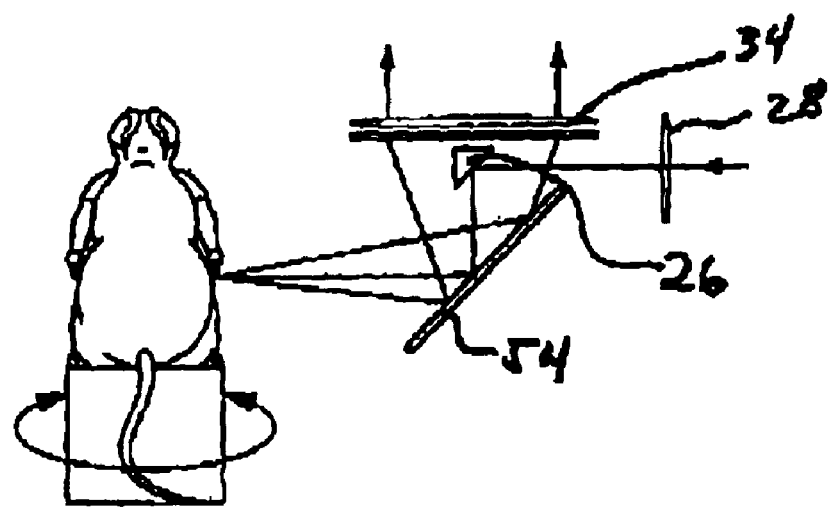
FIG. 6 is a schematic representation of an embodiment of the system of the invention in which the optical components are fixed and the mammal is rotated to acquire data for tomographic imaging.

In one embodiment, the illumination and collection optics are mounted on a movable gantry system 52 which turns around the animal (FIG. 5). In this particular embodiment, the tray preferably exhibits an "I" shape. This particular shape facilitates data acquisition as the illumination and collection optics is rotated around the region of interest (for example: torso region) while allowing the animal to be comfortably supported. With this configuration, angular displacements of an amplitude substantially equals to 360 degrees are possible. In a further embodiment, the mammal may be rotated instead of the gantry. The mammal may be maintained on the tray by attaching its legs to the tray. Rotation around the cranio-caudal axis of the body by 360° is possible. This design configuration can reduce weight, volume and complexity compared to the moveable gantry system.

In yet another embodiment the mammal can be rotated along the cranio-caudal axis while sitting. The animal is positioned on the stage such that the region of interest is kept straight by softly supporting its head. These designs allow the animal to be scanned over almost 360°. It will b appreciated that the optics may be modified to adapt it to the different tomographic configurations. For example, mirror 54 in the "sitting" configuration provides a convenient way of directionally propagating the light.

The acquisition of optical data at a plurality of angles around the animal may result in appreciable variations in the distance between the surface of the ROI and the collection optics because of the irregular contour of the animal. Accordingly image reconstruction may be improved by the use of an auto-focus system and by obtaining a profile of the scanned regions. In this respect, the system may also comprise means to determine the volumetric profile of the animal. In one embodiment, the volumetric profile can be determined by scanning the animal with a laser beam directed substantially perpendicularly to the animal. By simultaneously acquiring an image of the laser beam at the surface of the animal with a video camera placed at an angle to the laser path, the volumetric profile may be determined. The animal may be scanned by moving the tray. It will be appreciated that the volumetric profile thus obtained provides spatial information useful for image reconstruction and display.

While the imaging of biological tissue can rely on the natural optical properties of the endogenous molecules for providing optical contrast, exogenous molecules may be introduced in the tissue to provide additional contrast. In this respect, exogenous chromophores as well as fluorophores may be used. Furthermore the biodistribution of such contrast agents can be followed using the method and system of the present invention. In one advantageous embodiment the biodistribution can be followed over time thereby producing pharmacokinetics data.

The optics as well as the source can be arranged to illuminate and detect light at one or more wavelengths as is described supra. This property can be exploited to follow the pharmacokinetics of two or more fluorophores and/or chromophores. In particular, the source and associated optics can be arranged to illuminate at an excitation wavelength of a fluorophore while the detector and associated optics can be arranged to detect light at an emission wavelength of the fluorophore.

The embodiment(s) of the invention described above is(are) intended to be exemplary only. The scope of the invention is therefore intended to be limited solely by the scope of the appended claims.

We claim:

1. A method for collecting optical data for use in time resolved optical imaging of an animal, the method comprising:
   i) positioning said animal for data acquisition through free-space optics
   ii) directionally propagating through see-space optics a pulsed light beam of a selected intensity to illuminate a one or more wavelength a plurality of predetermined illumination points in a region of interest of the animal;

iii) selectively collecting, through free-space optics, light emanating from a plurality of predetermined collection points;

iv) directionally propagating through free-space optics the collected light towards a detector;

v) measuring, at one or more wavelength, the collected light at the detector to produce a time resolved optical signal for one or more illumination points/collection points configuration; and wherein light emanating from points other than the predetermined collection points is optically excluded from detection.

2. The method as claimed in claim 1, wherein the time resolved optical imaging is time domain (TD) imaging and wherein the time resolved optical signal is detected such as to generate information related to a temporal point spread function (TPSF).

3. The method as claimed in claim 2, wherein the step of measuring comprises detecting the collected light using time correlated single photon counting approach.

4. The method as claimed in claim 3, wherein each illumination point is illuminated by a plurality of pulses.

5. The method as claimed in claim 4, wherein the step of illuminating comprises adjusting the intensity of the light beam such as to avoid distortions caused by electronic dead-time losses.

6. The method as claimed in claim 5, wherein the intensity is adjusted by varying the source intensity.

7. The method as claimed in claim 6, wherein the intensity is adjusted with filters.

8. The method as claimed in claim 1, wherein the optical signal is detected at two or more wavelengths simultaneously.

9. The method as claimed in claim 1 wherein the optical signal is detected at two or more wavelengths sequentially.

10. The method as claimed in claim 1, wherein the illumination points are illuminated in a raster scan fashion.

11. The method as claimed in claim 1, wherein the collection points are located at a fixed distance from the illumination points to provide optical signal for topographic imaging.

12. The method as claimed in claim 11, wherein the distance is about 3 mm.

13. The method as claimed in claim 1, wherein two or more collection points are collected for each illumination point to provide optical data for tomographic imaging.

14. The method as claimed in claim 13, wherein at least two of the 2 or more collection points are collected simultaneously.

15. The method as claimed in claim 1, wherein detection is effected at a wavelength different from that of illumination.

16. The method as claimed in claim 1, wherein the region of interest of the animal comprises one or more fluorophores and wherein the detection wavelength corresponds to an emission wavelength of the one or more fluorophores and the illumination wavelength corresponds to an excitation wavelength of the one or more fluorophores.

17. The method as claimed in claim 16, wherein both the excitation and emission wavelength are detected.

18. The method as claimed in claim 2, wherein the TPSF is integrated to provide attenuation measurement.

19. The method as claimed in claim 1, wherein optical data from a plurality of regions of interest are collected during a single session.

20. The method as claimed in claim 19, wherein the plurality of regions of interest comprises a whole body of an animal.

21. The method as claimed in claim 1 wherein said animal is controllably heated.

22. A system for collecting optical data for use in time resolved optical imaging of an animal, the system comprising:

i) one or more pulsed light source of selected intensity for providing a light beam at one or more wavelengths;

ii) illuminating optic components for directionally propagating the beam through free space optics such that a region of interest of the biological tissue is illuminated at a plurality of illumination points thereby injecting light into the animal;

iii) collecting optic components for collecting through free space optics light re-emitted at a plurality of predetermined collection points in the region of interest such that light emanating from points other than the predetermined collection points is optically excluded from detection, and for directionally propagating, through free space optics, the collected light; and iv) a time domain detector for detecting the collected light.

23. The system as claimed in claim 22, wherein the one or more light sources are variable intensity light sources.

24. The system as claimed in claim 23, wherein the variable intensity light sources are lasers.

25. The system as claimed in claim 24, wherein the illuminating optic components comprise at least one moveable mirror for directing the beam to the plurality of illumination points.

26. The system as claimed in claim 25, wherein the moveable mirror is a mirror galvanometer.

27. The system as claimed in claim 26 further comprising a thin angled mirror located optically downstream of the mirror galvanometer.

28. The system as claimed in claim 27, wherein a lens is positioned between the mirror galvanometer and the thin angled mirror and optically coupled therewith to provide a telecentric imaging configuration.

29. The system as claimed in claim 28, wherein the collecting optic components comprise a lens located above the region of interest and having a focal point coincident with the collection point.

30. The system as claimed in claim 29, wherein the collecting optic components further comprise a mirror galvanometer for directing the collected light to the detector.

31. The system as claimed in claim 30, wherein the mirror galvanometers of the illumination optic and collection optic are synchronized so as to provide a fixed distance between the illumination points and respective detection points.

32. The system as claimed in claim 31, wherein the illumination optics, the detection optics and the source are part of a gantry that can be rotated around the animal.

33. The system as claimed in claim 30, wherein the mirror galvanometers of the illumination optic and collection optic are independently adjustable so as to provide a variable distance between the illumination points and respective detection points.

34. The system as claimed in claim 33, wherein the illumination optics, the detection optics and the source are part of a gantry that can be rotated around the animal.

35. The system as claimed in claim 23, further comprising a translational stage for moving a tray in a plane perpendicular to the illuminating beam wherein the tray is for supporting an animal.

36. The system as claimed in claim 35, wherein the tray is controllably heated to a desired temperature suitable for said animal.

37. The system as claimed in claim 22, wherein the detector is a time correlated single photon counting detector.

38. The system as claimed in claim 22, wherein the detector is a time gated ICCD.

39. The system as claimed in claim 22, wherein the animal, the optical components and the detector are contained in an enclosure.

40. The system as claimed in claim 39, wherein the enclosure is light tight.

* * * * *